US011077030B2

(12) United States Patent
Milora et al.

(10) Patent No.: US 11,077,030 B2
(45) Date of Patent: *Aug. 3, 2021

(54) SUNSCREEN FORMULATION

(71) Applicant: FALLIEN COSMECEUTICALS, LTD., Norristown, PA (US)

(72) Inventors: David J. Milora, Blue Bell, PA (US); Harry Fallick, Wayne, PA (US)

(73) Assignee: FALLIEN COSMECEUTICALS, LTD., Norristown, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/581,998

(22) Filed: Sep. 25, 2019

(65) Prior Publication Data
US 2020/0016047 A1 Jan. 16, 2020

Related U.S. Application Data

(63) Continuation of application No. 15/856,190, filed on Dec. 28, 2017, now Pat. No. 10,588,832, which is a (Continued)

(51) Int. Cl.
A61K 8/04 (2006.01)
A61K 8/60 (2006.01)
(Continued)

(52) U.S. Cl.
CPC ............ A61K 8/046 (2013.01); A61K 8/0241 (2013.01); A61K 8/19 (2013.01); A61K 8/27 (2013.01); A61K 8/29 (2013.01); A61K 8/37 (2013.01); A61K 8/375 (2013.01); A61K 8/4993 (2013.01); A61K 8/60 (2013.01); A61K 8/731 (2013.01); A61K 8/8147 (2013.01); A61K 8/8152 (2013.01); A61K 8/8176 (2013.01);
(Continued)

(58) Field of Classification Search
CPC ............ A61K 2800/21; A61K 2800/52; A61K 8/0241; A61K 8/046; A61K 8/19; A61K 8/27; A61K 8/29; A61K 8/37; A61K 8/375; A61K 8/4993; A61K 8/60; A61K 8/731; A61K 8/8147; A61K 8/8152; A61K 8/8176; A61K 8/85; A61K 8/86; A61K 8/87; A61Q 17/04
USPC ........................................................ 434/401
See application file for complete search history.

(56) References Cited

U.S. PATENT DOCUMENTS 4,891,213 A 1/1990 Gordon et al.
6,159,481 A 12/2000 Fallick
(Continued)

OTHER PUBLICATIONS

Federal Register vol. 64, No. 98 pp. 27666-93; published Friday May 21, 1999.
(Continued)

Primary Examiner — Johann R Richter
Assistant Examiner — Courtney A Brown
(74) Attorney, Agent, or Firm — Medler Ferro Woodhouse & Mills PLLC

(57) ABSTRACT

The present application relates to sunscreen formulations, including foamable sunscreen formulations, that comprise zinc oxide and titanium dioxide particles, suitably in the size range of about 1-100 nm. The compositions suitably produce a minimal residual whitening effect when applied to a skin surface.

20 Claims, 1 Drawing Sheet

Related U.S. Application Data continuation of application No. 15/387,709, filed on Dec. 22, 2016, now Pat. No. 10,154,946, which is a continuation of application No. 14/539,217, filed on Nov. 12, 2014, now Pat. No. 9,561,159, which is a continuation of application No. 13/648,707, filed on Oct. 10, 2012, now Pat. No. 8,911,754.

(60) Provisional application No. 61/545,848, filed on Oct. 11, 2011.

(51) Int. Cl.
| | | |
|---|---|---|
| *A61Q 17/04* | (2006.01) | |
| *A61K 8/29* | (2006.01) | |
| *A61K 8/37* | (2006.01) | |
| *A61K 8/49* | (2006.01) | |
| *A61K 8/73* | (2006.01) | |
| *A61K 8/81* | (2006.01) | |
| *A61K 8/86* | (2006.01) | |
| *A61K 8/02* | (2006.01) | |
| *A61K 8/27* | (2006.01) | |
| *A61K 8/19* | (2006.01) | |
| *A61K 8/85* | (2006.01) | |
| *A61K 8/87* | (2006.01) | |

(52) U.S. Cl.
CPC ............... *A61K 8/85* (2013.01); *A61K 8/86* (2013.01); *A61K 8/87* (2013.01); *A61Q 17/04* (2013.01); *A61K 2800/21* (2013.01); *A61K 2800/52* (2013.01)

(56) References Cited

U.S. PATENT DOCUMENTS

| | | | |
|---|---|---|---|
| 6,436,376 B1 | 8/2002 | Hansenne et al. | |
| 6,730,288 B1 | 5/2004 | Abram | |
| 6,869,596 B1 | 3/2005 | Knowland et al. | |
| 7,204,973 B2 | 4/2007 | Goppel et al. | |
| 8,309,063 B2 | 11/2012 | Sengupta et al. | |
| 8,795,696 B2 | 8/2014 | Milora et al. | |
| 8,911,754 B2 | 12/2014 | Milora et al. | |
| 9,561,159 B2 | 2/2017 | Milora et al. | |
| 10,154,946 B2 | 12/2018 | Milora et al. | |
| 2003/0072782 A1 | 4/2003 | Friel et al. | |
| 2004/0241105 A1* | 12/2004 | Riedel .................... A61K 8/731 424/47 |
| 2005/0036961 A1 | 2/2005 | Hansenne et al. | |
| 2005/0079142 A1 | 4/2005 | Brunckhorst et al. | |
| 2005/0129631 A1 | 6/2005 | Goppel et al. | |
| 2005/0142080 A1 | 6/2005 | Goppel et al. | |
| 2005/0186147 A1* | 8/2005 | Tamarkin ................ A61K 9/12 424/47 |
| 2006/0223737 A1 | 10/2006 | Sebillotte-Arnaud et al. | |
| 2006/0280702 A1 | 12/2006 | Sengupta et al. | |
| 2007/0224138 A1 | 9/2007 | Gibbons | |
| 2008/0260655 A1 | 10/2008 | Tamarkin et al. | |
| 2010/0129303 A1 | 5/2010 | Dueva-Koganov et al. | |
| 2011/0150792 A1 | 6/2011 | Shao et al. | |
| 2011/0206624 A1* | 8/2011 | Bandyopadhyay ...... A61K 8/35 424/59 |
| 2012/0093737 A1 | 4/2012 | Wang | |
| 2015/0071975 A1 | 3/2015 | Milora et al. | |
| 2018/0116917 A1 | 5/2018 | Milora et al. | |
| 2018/0168950 A1 | 6/2018 | Milora et al. | |

OTHER PUBLICATIONS

International Search Report and Written Opinion of the International Searching Authority in International Application No. PCT/US2012/059519, dated Dec. 6, 2012.

Non-final Office Action in U.S. Appl. No. 13/646,717, dated Jun. 20, 2013.

Non-final Office Action in U.S. Appl. No. 13/648,707, dated Dec. 4, 2013.

Final Office Action in U.S. Appl. No. 13/646,717, dated Dec. 11, 2013.

Notice of Allowance in U.S. Appl. No. 13/468,717, dated Apr. 3, 2014.

Non-final Office Action in U.S. Appl. No. 15/387,709, dated Oct. 3, 2017.

Final Office Action in U.S. Appl. No. 15/387,709, dated Jan. 24, 2018.

Non-final Office Action issued in U.S. Appl. No. 15/892,516, dated Jul. 30, 2019.

Renée Rouleau, "Chemical Vs. Physical Sunscreens: Pros and Cons," first published Jul. 9, 2015, updated Dec. 1, 2017. <http://blog.reneerouleau.com/chemical-vs-physical-sunscreens-pros-cons>, accessed May 22, 2018.

http://www.cosdna.com/eng/1213f410120.html (available on line Aug. 31, 2009), accessed Jun. 4, 2013.

http://www.cosdna.com/eng/42f67e10121.html (available on line Aug. 30, 2009), accessed Jun. 4, 2013.

http://www.cosdna.com/eng/bbc80b10122.html (available online Aug. 31, 2009), accessed Jun. 4, 2013.

* cited by examiner

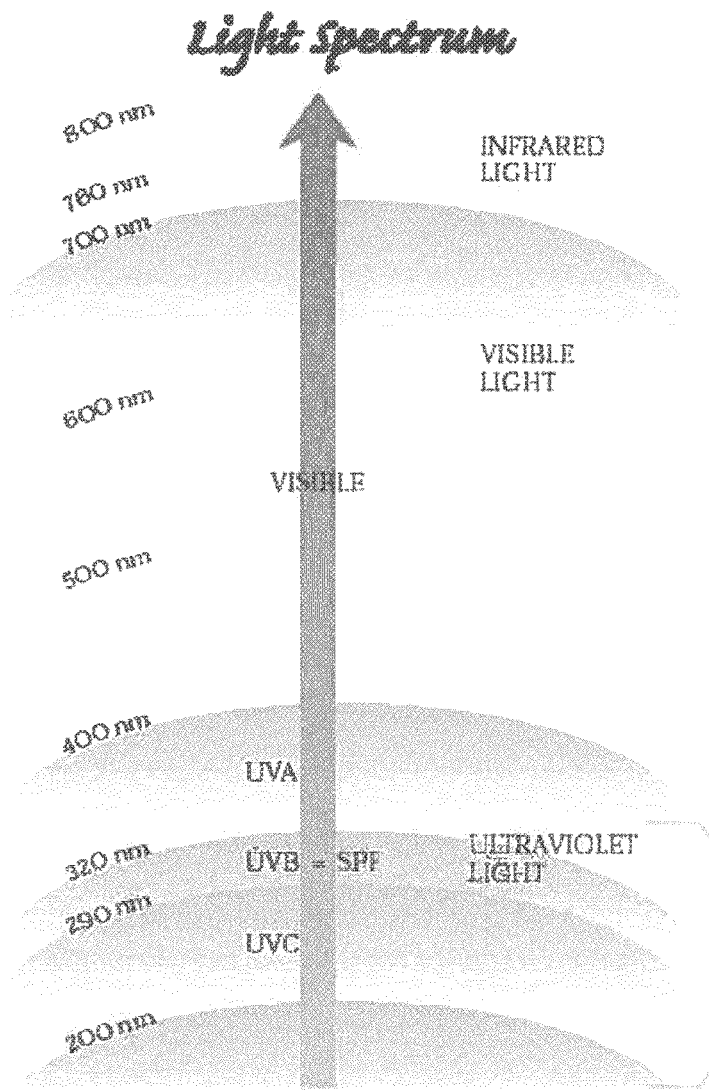

SUNSCREEN FORMULATION

CROSS REFERENCE TO RELATED APPLICATIONS

The present application is a continuation of U.S. patent application Ser. No. 15/856,190, filed Dec. 28, 2017, pending, which is a continuation of U.S. patent application Ser. No. 15/387,709, filed Dec. 22, 2016, now U.S. Pat. No. 10,154,946, issued Dec. 18, 2018, which is a continuation of U.S. patent application Ser. No. 14/539,217, filed Nov. 12, 2014, now U.S. Pat. No. 9,561,159, issued Feb. 7, 2017, which is a continuation of U.S. patent application Ser. No. 13/648,707, filed Oct. 10, 2012, now U.S. Pat. No. 8,911,754, issued Dec. 16, 2014, which claims the benefit of U.S. Provisional Patent Application No. 61/545,848, filed Oct. 11, 2011, the disclosures of each of which are incorporated by reference herein in their entireties.

BACKGROUND OF THE INVENTION

Field of the Invention

The present application relates to sunscreen formulations, including foamable sunscreen formulations, that comprise zinc oxide and titanium dioxide particles, suitably in the size range of about 1-100 nm. The compositions suitably produce a minimal residual whitening effect when applied to a skin surface.

Background of the Invention

More than 1 million Americans are diagnosed with skin cancer each year, and many more with precancerous conditions. These numbers continue to increase, not only in the United States, but worldwide. Several factors appear to be responsible for this alarming rise in skin cancer. The continual erosion of the earth's ozone layer due to pollution results in less available ozone protection than was afforded previous generations. Also, unlike previous generations, today there are over 400 medications prescribed that leave patients with an increased sensitivity to sun exposure and a heightened susceptibility to sun damage. Longer lifespan is also a contributing factor. Greater awareness, increased patient concern and better diagnosis may help to decrease this alarming rise in the rate of skin cancer.

Perhaps the most important factor in the rise of skin cancer rates is increased exposure to the ultraviolet A (UVA) wavelength, which is typically defined as 320 to 400 nanometers (nm) in the light spectrum (see FIG. 1). Previously thought of as harmless, this wavelength range is now known to contribute significantly to skin damage, skin cancer, DNA damage and Immune system suppression. UVA rays penetrate the skin deeper and, unlike UVB rays (defined as the range of 290 to 320 nm, which cause initial redness and burning), damage from UVA rays is not immediately detected. Because UVA rays remain constant throughout the year and during the day, we are exposed to them continuously.

Sunscreen products are traditionally delivered to the skin in the form of creams, lotions, gels and more recently, by means of aerosol sprays or mists. Delivery of particles of titanium dioxide and/or zinc oxide by means of a spray or mist may create an inhalation hazard during application across the open air. Consequently, aerosol spray sunscreens currently use organic chemical sunscreen filters, which are solubilized in the inactive ingredients prior to delivery to the skin, but the possibility of inhalation of the sunscreen product remains.

There exists therefore a need for a readily dispensed sunscreen formulation that is easily applied to the skin, reduces or eliminates possible product inhalation, and maintains a uniform composition throughout the formulation, particularly when utilizing particulate sunscreens, e.g., zinc oxide and/or titanium dioxide.

SUMMARY OF PREFERRED EMBODIMENTS

The needs identified above are met by the present application.

In embodiments, foamable sunscreen formulations are provided. Exemplary formulations comprise zinc oxide particles, titanium dioxide particles, about 0.1% to about 10% emulsion stabilizer, about 0.1% to about 25% skin conditioner, about 0.1% to about 10% emulsifier, about 0.1% to about 10% suspending agent and the remainder water. Suitably, the amounts and particle sizes of the zinc oxide and the titanium dioxide are selected so as to produce a minimal residual whitening effect when applied to a skin surface.

In embodiments, the emulsion stabilizer is a naturally derived gum or a modified gum or natural mineral. Exemplary emulsion stabilizers include acacia, cellulose, crystalline cellulose, gellan, guar, locust (carob) bean, xanthan gums, magnesium aluminum silicate, bentonite and hectorite clays and/or combinations thereof.

Exemplary skin conditioners/emollients include adipate esters, alkyl benzoates, fatty acid esters of $C_8$ or greater, esterified erucates, laurates, neopentanoates, salicylates, stearates, triglycerides, carbonates, glycols, glycerin, mineral oils and combinations thereof.

Exemplary emulsifiers include polysorbates, fatty acids and their alkaline salts, ethoxylated fatty acids and their alkaline salts, and substituted glucosides. Exemplary suspending agents typically include hydroxystearic acid, polyhydroxystearic acid, sodium polyacrylate polymers, methyl methacrylate crosspolymers and combinations thereof.

In embodiments, the formulations further comprise about 0.1% to about 10% film former for added water resistance, including film formers such alkyl methacrylate acid copolymers, acrylates/$C_{12-22}$ alkyl methacrylate copolymer, acrylates/octylacrylamide copolymer, polyamide-3, polyurethane-2, polyurethane-34, polyurethane-35, and co-polymers of each, vinyl pyrollidone/eicosene copolymers, tricontanyl/polyvinyl pyrollidone, dimethicone substituted polyacrylates and combinations thereof.

In further embodiments, foamable sunscreen formulations are provided chat comprise about 1% to about 25% zinc oxide particles having a primary particle size of less than about 50 nm, about 1% to about 25% titanium dioxide particles having a primary particle size of less than about 50 nm, about 0.1% to about 5% emulsion stabilizer, about 0.1% to about 25% skin conditioner, about 1% to about 10% emulsifier, about 0.1% to about 10% suspending agent and the remainder water.

In additional embodiments, provided herein is a foamable sunscreen formulation comprising about 9% to about 11% zinc oxide particles having a primary particle size of about 20 nm, about 2% to about 4% titanium dioxide particles having a primary particle size of about 30 nm, about 0.5% to about 5.0% emulsion stabilizer, about 15% to about 25% skin conditioner, about 2.5% to about 4.5% emulsifier, about 3.5% to about 5.5% suspending agent about 1% to about 2.5% film former and the remainder water.

In still further embodiments, a foamable sunscreen formulation is provided herein that comprises about 10% zinc oxide particles having a primary particle size of about 20 nm, about 3% titanium dioxide particles having a primary particle size of about 30 nm, about 1% microcrystalline cellulose and about 0.2% cellulose gum, about 16% $C_{12-15}$ alkyl benzoate, about 1% octyldodecyl neopentanoate, about 1% butyl octyl salicylate, about 1.2% glyceryl stearate, about 0.5% ceteareth-20, and about 2% polysorbate 80, about 1.8% polyhydroxystearic acid and about 2.7% methyl methacrylate crosspolymer, about 0.8% polyurethane-2, about 0.3% polymethyl methacrylate and about 0.6% tricontanyl PVP film and about 50% to about 60% water and a preservative.

Also provided are methods of preventing sun damage to a patient's skin surface, comprising applying the foamable sunscreen formulations described herein to a patient's skin.

Further embodiments, features, and advantages of the embodiments, as well as the structure and operation of the various embodiments, are described in detail below.

DESCRIPTION OF THE FIGURES

FIG. 1 shows a diagram of the light spectrum from sunlight.

DETAILED DESCRIPTION OF PREFERRED EMBODIMENTS

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. It should be understood that use of the term "about" also includes the specifically recited amount.

Technical and scientific terms used herein have the meaning commonly understood by one of skill in the art to which the present application pertains, unless otherwise defined. Reference is made herein to various methodologies and materials known to those of skill in the art.

In embodiments, the application provides foamable sunscreen formulations. In exemplary embodiments, the formulations comprise zinc oxide particles and/or titanium dioxide particles, and suitably both zinc oxide and titanium dioxide particles.

As used herein, the term "foamable" or "foam" as it relates to a formulation refers to an aqueous emulsion system, that upon actuation with an aerosol, produces a stabilized, homogenous, expandable composition that breaks easily upon shearing. The terms foams and foamable formulations are used interchangeably throughout. Suitably, the foams and foamable formulations described herein are for application to a skin surface of a mammal, suitably a human.

As used herein the term "sunscreen" refers to a formulation that protects the skin from sunburn and erythema by absorbing, reflecting, filtering, scattering and/or blocking ultraviolet (UV) radiation.

Ultraviolet (UV) radiation includes, UVA, UVB, UVC and combinations of UVA, UVB and UVC light. See FIG. 1.

In exemplary embodiments, the formulations described herein further comprise one or more emulsion stabilizers, one or more skin conditioners, one or more emulsifiers, one or more suspending agents and water.

Unless otherwise indicated, when referring to an amount of a component of the formulations, the percent (%) of a component refers to the weight percent (weight %; wt %) of the component in the formulation, where the total amounts of all components equal 100% by weight (100 weight %).

Suitably, the amount of emulsion stabilizer (i.e., one or more emulsions stabilizers) in the formulations is about 0.01% to about 20%, more suitably about 0.05% to about 15%, about 0.05% to about 10%, about 0.05% to about 8%, about 0.08% to about 7%, about 0.09% to about 6%, about 0.1% to about 5%, about 0.3% to about 5%, about 0.5% to about 5%, or about 0.5%, about 0.6%, about 0.7%, about 0.8%, about 0.9%, about 1%, about 1.5%, about 2%, about 2.5%, about 3%, about 3.5%, about 4%, about 4.5% or about 5% emulsion stabilizer, including all values and ranges within these ranges.

Suitably, the amount of skin conditioner (i.e., one or more skin conditioners) in the formulation is about 0.01% to about 30%, more suitably about 0.05% to about 25%, about 0.1% to about 25%, about 1% to about 25%, about 5% to about 25%, about 10% to about 25%, about 15% to about 25%, about 10%, about 11%, about 12%, about 13%, about 14%, about 15%, about 16%, about 17%, about 18%, about 19%, about 20%, about 21%, about 22%, about 23%, about 24% or about 25%, including all ranges and values within these ranges.

Suitably, the amount of emulsifier (i.e., one or more emulsifiers) in the formulations is about 0.01% to about 20%, more suitably about 0.05% to about 20%, about 0.1% to about 20%, about 0.1% to about 15%, about 0.1% to about 10%, 0.5% to about 10%, about 1% to about 10%, about 2% to about 5%, about 2.5% to about 4.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5% or about 10%, including all values and ranges within these ranges.

Suitably, the amount of suspending agent (i.e., one or more suspending agents) is about 0.05% to about 20%, more suitably about 0.1% to about 20%, about 0.1% to about 15%, about 0.1% to about 10%, about 1% to about 10%, about 2% to about 6%, about 3.5% to about 5.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5% or about 10%, including all values and ranges within these ranges.

Suitably, the remainder (i.e., qs) of the formulation compositions described herein is purified/sterilized/deionized water. It is routine for those of ordinary skill in the art to determine the required weight percent of water necessary to make up the remainder of the composition so as to yield 100% by weight, taking into consideration the amounts of the other ingredients.

As described throughout, in embodiments, the amounts and particle sizes of the zinc oxide and the titanium dioxide in the formulations are selected so as to produce a minimal residual whitening effect when the formulations are applied to a skin surface. The term "minimal residual whitening effect" is used herein to mean that, the formulations when evenly spread onto a skin surface at a concentration of between 1-3 mg/cm$^2$, more suitably at a concentration of 2 mg/cm$^2$, for example as set forth in the in the SPF Test Parameters, Federal Register, vol. 76, no. 117, pages 35644-35645 (Jul. 17, 2011) (the disclosure of which is incorporated by reference herein in its entirety), are not visible on the skin surface to the naked eye, i.e., they do not produce a whitening effect that is visible to the naked eye.

In embodiments, the present application provides formulations that comprise zinc oxide and titanium dioxide, with specifically selected particle sizes and amounts, so as to produce a minimal residual whitening effect when the formulations are applied to a skin surface. Selection of the particle size and the amounts of the zinc oxide and titanium dioxide is carried out by preparing the desired formulations with the desired particle sizes and amounts of the zinc oxide and titanium dioxide, applying the formulations to a skin surface as described herein, and determining if the formulation leaves a residual whitening effect on the skin surface.

Sub-micron scale (particles less than 1 μm in diameter) titanium dioxide works by absorbing, reflecting and scattering UVB and some UVA radiation. Zinc oxide provides a block for ultraviolet light (UVB/UVA). It also reflects infrared from the skin, as does titanium dioxide. However, zinc oxide's ability to protect in the long UVA range, (300-400 nm) is much higher than titanium dioxide. Zinc oxide absorbs, rather than scatters, most UVA, while titanium dioxide primarily scatters these wavelengths. Thus, formulated in combination with titanium dioxide, zinc oxide "closes the window" in the UVA range. Zinc oxide works to both complement titanium dioxide's protection and extend photoprotection to the skin where titanium dioxide may be insufficient.

Suitably, in embodiments, the formulations described herein comprise about 1% to about 25% zinc oxide particles having a primary particle size of less than about 50 nm. In exemplary embodiments, the formulations comprise about 3% to about 20% zinc oxide particles, more suitably about 5% to about 15%, about 7% to about 12%, about 9% to about 11%, or about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19% or about 20%, zinc oxide particles.

Suitably, in embodiments, the primary particle size of the zinc oxide particles is less than about 50 nm. As used herein, "primary particle size" is defined as the size (suitably diameter) of disperse, individual particles of a material without any agglomeration of or between particles. Suitably, in embodiments, the zinc oxide particles have a primary particle size that is about 10 nm to about 40 nm, more suitably about 10 nm to about 30 nm, or about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 am, about 28 nm, about 29 nm or about 30 nm, including primary particle sizes and ranges within these ranges.

Suitably, in embodiments, the formulations described herein comprise about 1% to about 25% titanium dioxide particles having a primary particle size of less than about 50 nm. In exemplary embodiments, the formulations comprise about 3% to about 20% titanium dioxide particles, more suitably about 5% to about 15, about 7% to about 12%, about 9% to about 11%, or about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19% or about 20%, titanium dioxide particles.

Suitably, in embodiments, the primary particle size of the titanium dioxide particles is less than about 50 nm. Suitably, the titanium dioxide particles have a primary particle size that is about 10 nm to about 40 nm, more suitably about 20 nm to about 40 nm, or about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 39 nm, about 40 nm, including primary particle sizes and ranges within these ranges.

In embodiments, the formulations described herein comprise either zinc oxide or titanium dioxide particles. In more suitable embodiments, the formulations comprise both zinc oxide and titanium dioxide particles.

As used herein an "emulsion stabilizer" refers to a composition that aids in keeping an emulsion from separating into its oil and aqueous components. In embodiments, the emulsion stabilizer utilized in the formulations described herein is a naturally derived gum or a modified gum or natural mineral. Exemplary emulsion stabilizers include, but are not limited to, acacia, cellulose, crystalline cellulose, gellan, guar, locust (carob) bean, xanthan, magnesium aluminum silicate, bentonite or hectorite clays and the like, including combinations thereof.

As used herein a "skin conditioner" refers to a composition that acts as a lubricant on the surface of the skin or a composition that increases the water content of the surface of the skin. Exemplary skin conditioners for use in the formulations include, but are not limited to, adipate esters, alkyl benzoates, fatty acid esters of $C_8$ or greater, esterified erucates, laurates, neopentanoates, salicylates, stearates, triglycerides, carbonates, glycols, glycerin, mineral oils and the like, including combinations thereof.

As used herein an "emulsifier" refers to a composition that aids in the formation of an oil in water, or a water in oil, emulsion. Exemplary emulsifiers for use in the formulations include, but are not limited to, polysorbates, ethoxylated fatty acids, fatty acids neutralized with sodium hydroxide, potassium hydroxide or amines, substituted glucosides, sodium lauryl and lauryl ether sulfates, ethoxylated esters, lecithin and lecithin derivatives and the like, including combinations thereof.

As used herein a "suspending agent" refers to a composition that modifies the interface between solid particles and a liquid medium to improve the particles' resistance to coming together and falling out of solution. Exemplary suspending agents for use in the formulations include, but are not limited to, hydroxy stearic acid, polyhydroxystearic acid, sodium polyacrylate polymers, methyl methacrylate crosspolymers and the like, including combinations thereof.

In embodiments, the formulations described herein further comprise a film former. Suitably, the amount of the film former (i.e., one or more film formers) is about 0.05% to about 20%, mores suitably about 0.1% to about 20%, about 0.1% to about 15%, about 0.1% to about 10%, about 1% to about 10%, about 2% to about 6%, about 3.5% to about 5.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5% or about 10%, including all values and ranges within these ranges.

As used herein a "film former" refers to a composition that dries to form a thin coating on the skin to impart water resistance. Exemplary film formers for use in the formulations include, but are not limited to, alkyl methacrylate acid copolymers, acrylates/$C_{10-30}$ alkyl methacrylate copolymer, acrylates/octylacrylamide copolymer, polyamide-3, polyurethates-2, polyurethanes-34, polyurethanes-35, vinyl pyrollidone/eicosene copolymer, tricontanyl/polyvinyl pyrollidone, dimethicone substituted polyacrylates and the like, including combinations thereof.

In additional embodiments, foamable sunscreen formulations are provided that comprise:
 about 1% to about 25% zinc oxide particles having a primary particle size of less than about 50 nm;
 about 1% to about 25% titanium dioxide particles having a primary particle size of less than about 50 nm;
 about 0.1% to about 10% emulsion stabilizer;
 about 0.1% to about 25% skin conditioner;
 about 1% to about 10% emulsifier;
 about 0.1% to about 10% suspending agent; and
 the remainder water.

As described herein, in embodiments, suitably the zinc oxide particles have a primary particle size of less than about 30 nm, more suitably about 20 nm, or about 10 nm. In suitable embodiments, the formulations comprise about 10% zinc oxide particles.

As described herein, in embodiments, suitably the titanium dioxide particles have a primary particle size of about 30 nm, more suitably about 20 nm. In embodiments, the formulations comprise about 3% titanium dioxide particles.

In embodiments, the emulsion stabilizers for use in the formulations include, but are not limited to, microcrystalline cellulose, cellulose gum and the like, including combinations thereof.

In embodiments, the skin conditioners for use in the formulations include, but are not limited to, $C_{12-15}$ alkyl benzoate, octyldodecyl neopentanoate, butyl octyl salicylate, caprylyl glycol, glycerin and the like, including combinations thereof.

In embodiments, the emulsifiers for use in the formulations include, but are not limited to, glyceryl stearate, ceteareth-20, polysorbate 80 and the like, including combinations thereof.

In embodiments, the suspending agents for use in the formulations include, but are not limited to, polyhydroxystearic acid, methyl methacrylate crosspolymer and the like, including combinations thereof.

As described herein, in embodiments, the formulations further comprise a film former, suitably about 0.5% to about 3%. Exemplary film formers for use in the formulations include, but are not limited to, polyurethane-2, polymethyl methacrylate, tricontanyl poly(vinyl pyrrolidone) (PVP) and the like, including combinations thereof.

In additional embodiments, the formulations further comprise iron oxide particles. By controlling the purity, particle size, temperature and rate of drying during manufacture, iron oxide particles exhibit a number of shades and tones of red, yellow, black and brown (and blends of these basic colors). These pigments, if incorporated at adequate concentration and properly dispersed in not only add color to the formulations, but can contribute significant protection to the skin over multiple wavelengths of light.

It has been determined that the addition of iron oxide particles having a primary particle size of less than about 50 nm results in the addition of a color tone to the formulations, further diminishing any residual whitening effect of the sunscreen formulations described herein by matching the color of the formulations with that of the color of a skin surface. The iron oxide particles can be of a single primary particle size that results in a single color, or can be combinations of various particle sizes, including particles that produce a red, yellow, brown and/or black color, resulting in a tone of the formulation that can be tailored to the desired color.

Suitably, in embodiments, the formulations described herein comprise about 0.01% to about 10% iron oxide particles having a primary particle size of less than about 50 nm. In embodiments, the formulations comprise about 0.03% to about 8%, about 0.05% to about 7%, about 0.05% to about 5%, about 0.1% to about 4%, about 0.1% to about 3%, about 0.1% to about 2%, about 0.1% to about 1%, about 0.05%, about 0.1%, about 0.15%, about 0.2%, about 0.25%, about 0.3%, about 0.35%, about 0.4%, about 0.45%, or about 0.5% iron oxide particles.

Suitably, in embodiments, the iron oxide particles have a primary particles size less than about 50 nm. Suitably, the iron oxide particles have a primary particle size that is about 10 nm to about 40 nm, more suitably about 10 nm to about 30 nm, or about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm or about 30 nm, including primary particle sizes and ranges within these ranges.

In additional embodiments, foamable sunscreen formulations are provided that comprise:
 about 9% to about 11% zinc oxide particles having a primary particle size of about 20 nm;
 about 2% to about 4% titanium dioxide particles having a primary particle size of about 30 nm;
 about 0.5% to about 10% emulsion stabilizer;
 about 15% to about 25% skin conditioner;
 about 2.5% to about 4.5% emulsifier;
 about 3.5% to about 5.5% suspending agent;
 about 1% to about 2.5% film former; and
 the remainder water.

In embodiments, the formulations comprise about 10% zinc oxide particles. In additional embodiments, the formulations suitably comprise about 3% titanium dioxide particles. In further embodiments, the formulations suitably comprise about 10% zinc oxide particles and about 3% titanium dioxide particles.

Suitably, the emulsion stabilizers for use in the formulations are microcrystalline cellulose, cellulose gum and combinations thereof. Suitably, the skin conditioners for use in the formulations are $C_{12-15}$ alkyl benzoate, octyldodecyl neopentanoate, butyl octyl salicylate, caprylyl glycol, glycerin and combinations thereof. Suitably, the emulsifiers are glyceryl stearate, ceteareth-20, polysorbate 80 and combinations thereof. Suitably, the suspending agents are polyhydroxystearic acid, methyl methacrylate crosspolymer and combinations thereof. Suitably, the film formers are polyurethane-2, polymethyl methacrylate, tricontanyl poly(vinyl pyrollidone) (PVP) and combinations thereof.

In additional embodiments, the formulations further comprise about 0.05% to about 0.5% iron oxide particles having a primary particle size of less than about 50 nm.

In further embodiments, the present application provides foamable sunscreen formulations comprising:
- about 10% zinc oxide particles having a primary particle size of about 20 nm;
- about 3% titanium dioxide particles having a primary particle size of about 30 nm;
- about 1% microcrystalline cellulose and about 0.2% cellulose gum; about 16% $C_{12-15}$ alkyl benzoate, about 1% octyldodecyl neopentanoate, about 1% butyl octyl salicylate;
- about 1.2% glyceryl stearate, about 0.5% ceteareth-20, and about 2% polysorbate 80;
- about 1.8% polyhydroxystearic acid and about 2.7% methyl methacrylate crosspolymer;
- about 0.8% polyurethane-2, about 0.3% polymethyl methacrylate and about 0.6% tricontanyl PVP film; and
- about 50% to about 60% water and a preservative.

Suitably, such formulations further comprise about 0.05% to about 1.0% iron oxide particles having a primary particle size of less than about 50 nm.

In further embodiments, provided herein are foamable sunscreen formulations comprising some portion of particles that have a primary particle size larger than about 100 nm. In such embodiments, pigments are used to result in a formulation that still produces a minimal residual whitening effect, even though the formulations comprise particles that are larger than 100 nm, by coloring the formulations to match the color of a skin surface.

In embodiments, foamable sunscreen formulations are provided that comprise active particles comprising zinc oxide particles and titanium dioxide particles. The formulations also comprise about 0.1% to about 10% emulsion stabilizer, about 0.1% to about 25% skin conditioner, about 0.1% to about 10% emulsifier, about 0.1% to about 10% suspending agent, one or more pigments and the remainder water. Suitably the formulations comprise at least about 5 wt % of the active particles have a primary particle size greater than about 100 nm. As described herein, suitably the formulation produces a minimal residual whitening effect when applied to a skin surface.

As utilized herein, "active particles" is used to mean particles that either absorb, reflect and/or scatter UVA and/or UVB light, so as to produce a formulation that protects the skin from sunburn and erythema by absorbing, reflecting, filtering, scattering and/or blocking ultraviolet (UV) radiation. Suitably, active particles comprise zinc oxide and/or titanium dioxide particles.

In embodiments, at least 1%, suitably at least 5% of the active particles have a primary particle size greater than about 100 nm. That is, at least 1% by weight of the total weight of active particles utilized in a formulation have a primary particle size greater than about 100 nm. More suitably, at least about 10% of the active particles have a primary particle size greater than 100 nm, or at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the active particles have a primary particle size greater than about 100 nm.

In embodiments, at least about 5% of the active particles have a primary particle size greater than about 100 nm, suitably greater than about 200 nm, greater than about 300 nm, greater than about 400 nm, greater than about 500 nm, greater than about 600 nm, greater than about 700 nm, greater than about 800 nm, greater than about 900 nm, or about 1 .mu.m. Suitably, an upper limit for the primary particle size is about 800 nm to about 900 nm, generally where the formulations begin to feel gritty or grainy when applied to a skin surface. Thus, in embodiments, the primary particle size is about 100 nm to about 900 nm, about 100 nm to about 800 nm, about 100 nm to about 700 nm, about 100 nm to about 600 nm, about 100 nm to about 500 nm, about 100 nm to about 400 nm, about 100 nm to about 300 nm, or about 100 nm to about 200 nm, including values and ranges within these size ranges. For example, titanium dioxide particles can have a primary particle size of about 150 nm to about 10,000 nm, with a mean of about 1100 nm and zinc oxide particles can have a primary particle size of about 150 nm to about 550 nm, with a mean of about 380 nm.

In certain embodiments, the formulations comprise active particles comprising zinc oxide particles having a primary particle size greater than about 100 nm and titanium dioxide particles having a primary particle size less than about 50 nm in size. Titanium dioxide particles having a primary particle size less than about 50 nm in size are described herein.

In further embodiments, the formulations comprise active particles comprising titanium dioxide particles having a primary particle size greater than about 100 nm in size and zinc oxide particles having a primary particle size less than about 50 nm in size. Zinc oxide particles having a primary particle size less than about 50 nm are described herein.

In still further embodiments, the formulations comprise active particles comprising titanium dioxide particles having a primary particle size greater than about 100 nm in size and zinc oxide particles having a primary particle size greater than about 100 nm in size.

As described throughout, in exemplary embodiments, an exemplary emulsion stabilizer is a naturally derived gum or a modified gum or natural mineral, including an emulsion stabilizer selected from the group consisting of acacia, cellulose, crystalline cellulose, gellan, guar, locust (carob) bean, xanthan, magnesium aluminum silicate, bentonite or hectorite clays and/or combinations thereof.

Exemplary skin conditioners include those described throughout, such as adipate esters, alkyl benzoates, fatty acid esters of $C_8$ or greater, esterified erucates, laurates, neopentanoates, salicylates, stearates, triglycerides, carbonates, glycols, glycerin, mineral oils and combinations thereof. Exemplary emulsifiers include polysorbates, fatty acids and their alkaline salts, ethoxylated fatty acids and their alkaline salts of sodium hydroxide, potassium hydroxide and amines, substituted glucosides, sodium lauryl sulfate and lauryl ether sulfates, ethoxylated esters, lecithin and lecithin derivatives and combinations thereof.

In embodiments, exemplary suspending agents include hydroxy stearic acid, polyhydroxystearic acid, sodium polyacrylate polymers, methyl methacrylate crosspolymers and combinations thereof.

As described herein, the formulations can further comprise about 0.1% to about 10% film former, including alkyl methacrylate acid copolymers, acrylates/$C_{12-22}$ alkyl methacrylate copolymer, acrylates/octylacrylamide copolymer, polyamide-3, polyurethane-2, polyurethanes-34, polyurethanes-35, vinyl pyrollidone/eicosene copolymer, tricontanyl/polyvinyl pyrrolidone, dimethicone substituted polyacrylates and combinations thereof.

As utilized herein, the term "pigments" means one or more dyes, particles, elements, or other agents that are used to color, tint or otherwise modify the visual appearance of a formulation as it appears on a skin surface. Suitable pigments for use in the formulations described herein include, but are not limited to, iron oxide particles, aluminum powder, barium sulfate, various root extracts, mineral coloring agents, and various dyes.

Suitably, as described herein, the pigments utilized in the formulations are iron oxide particles having a primary particle size of less than about 50 nm. Use of iron oxide particles in the formulations comprising active particles having a primary particle size greater than about 100 nm, results in the addition of a color tone to the formulations, diminishing or removing any residual whitening effect of the sunscreen formulations by matching the color of the formulations with that of the color of a skin surface. The iron oxide particles can be of a single primary particle size that results in a single color, or can be combinations of various particle sizes, including particles that produce a red, yellow, brown and/or black color, resulting in a tone of the formulation that can be tailored to the desired color. Suitably the foamable sunscreen formulations comprise iron oxide particles comprising red iron oxide particles, yellow iron oxide particles or black iron oxide particles (i.e., iron oxide particles that result in these colors due to their particle size), and mixtures thereof. As described herein, the amount of iron oxide particles can be varied based on the desired coloration in the formulation, and suitably, the iron oxide particles are present at about 0.01 wt % to about 1 wt % in the formulations.

In further embodiments, a foamable sunscreen formulation is provided comprising: active particles comprising zinc oxide particles having a primary particle size of less than about 50 nm and titanium dioxide particles having a primary particle size of greater than about 100 nm;
  about 0.1% to about 10% emulsion stabilizer;
  about 0.1% to about 25% skin conditioner;
  about 1% to about 10% emulsifier;
  about 0.1% to about 10% suspending agent;
  iron oxide particles; and
  the remainder water.

As described herein, suitably at least about 5 wt % of the active particles are greater than about 100 nm in size, and the formulation produces a minimal residual whitening effect when applied to a skin surface.

Suitably, the emulsion stabilizer is selected from the group consisting of microcrystalline cellulose, cellulose gum and combinations thereof. Exemplary skin conditioners include $C_{12-15}$ alkyl benzoate, octyldodecyl neopentanoate, butyl octyl salicylate, caprylyl glycol, glycerin and combinations thereof. Suitable emulsifiers are elected from the group consisting of glyceryl stearate, ceteareth-20, polysorbate 80 and combinations thereof. Exemplary suspending agents are selected from the group consisting of polyhydroxystearic acid, methyl methacrylate crosspolymer and combinations thereof.

Suitably the formulations further comprise about 0.5% to about 3% film former, such as polyurethane-2, polymethyl methacrylate, tricontanyl poly(vinyl pyrollidone) (PVP) and combinations thereof.

As described herein, suitably at least about 20% of the active particles have a primary particle size greater than about 100 nm in size, more suitably at least about 50%, or at least about 75% of the active particles have a primary particle size greater than about 100 nm in size.

In embodiments, the iron oxide particles comprise red iron oxide particles, yellow iron oxide particles or black iron oxide particles, and mixtures thereof, suitably present at about 0.01 wt % to about 1 wt %.

Also provided are foamable sunscreen formulations comprising: active particles comprising titanium dioxide particles having a primary particle size of less than about 50 nm and zinc oxide particles having a primary particle size of greater than about 100 nm;
  about 0.1% to about 10% emulsion stabilizer;
  about 0.1% to about 25% skin conditioner;
  about 1% to about 10% emulsifier;
  about 0.1% to about 10% suspending agent;
  iron oxide particles; and
  the remainder water.

Suitably, at least about 5 wt % of the active particles have a primary particle size greater than about 100 nm, and wherein the formulation produces a minimal residual whitening effect when applied to a skin surface.

Exemplary components of the formulations and size ranges of the active particles are described herein.

Also provided are foamable sunscreen formulations comprising: active particles comprising titanium dioxide particles having a primary particle size of greater than about 100 nm and zinc oxide particles having a primary particle size of greater than about 100 nm;
  about 0.1% to about 10% emulsion stabilizer;
  about 0.1% to about 25% skin conditioner;
  about 1% to about 10% emulsifier;
  about 0.1% to about 10% suspending agent;
  iron oxide particles; and
  the remainder water.

Suitably the formulation produces a minimal residual whitening effect when applied.

In additional embodiments, foamable sunscreen formulations are provided comprising:
  active particles comprising zinc oxide particles having a primary particle size of less than about 50 nm and titanium dioxide particles having a primary particle size of greater than about 100 nm;
  about 1% microcrystalline cellulose and about 0.2% cellulose gum; about 16% $C_{12-15}$ alkyl benzoate, about 1% octyldodecyl neopentanoate, about 1% butyl octyl salicylate;
  about 1.2% glyceryl stearate, about 0.5% ceteareth-20, and about 2% polysorbate 80;
  about 1.8% polyhydroxystearic acid and about 2.7% methyl methacrylate crosspolymer;
  about 0.8% polyurethane-2, about 0.3% polymethyl methacrylate and about 0.6% tricontanyl PVP film;
  iron oxide particles comprising red iron oxide particles, yellow iron oxide particles or black iron oxide particles, and mixtures thereof and about 50% to about 60% water.

Suitably, at least about 5 wt % of the active particles have a primary particle size greater than about 100 nm in size, and the formulation produces a minimal residual whitening effect when applied to a skin surface.

In suitable embodiments, at least about 20% of the active particles have a primary particle size greater than about 100 nm, more suitably at least about 50% of the active particles have a primary particle size greater than about 100 nm, or at least about 75% of the active particles have a primary particle size greater than about 100 nm. Suitably the formulations comprise about 0.05% to about 1.0% iron oxide particles having a primary particle size of less than about 50 nm.

Also provide are foamable sunscreen formulations comprising:

active particles comprising titanium dioxide particles having a primary particle size of less than about 50 nm and zinc oxide particles having a primary particle size of greater than about 100 nm;
about 1% microcrystalline cellulose and about 0.2% cellulose gum; about 16% $C_{12-15}$ alkyl benzoate, about 1% octyldodecyl neopentanoate, about 1% butyl octyl salicylate;
about 1.2% glyceryl stearate, about 0.5% ceteareth-20, and about 2% polysorbate 80;
about 1.8% polyhydroxystearic acid and about 2.7% methyl methacrylate crosspolymer;
about 0.8% polyurethane-2, about 0.3% polymethyl methacrylate and about 0.6% tricontanyl PVP film;
iron oxide particles comprising red iron oxide particles, yellow iron oxide particles or black iron oxide particles, and mixtures thereof; and about 50% to about 60% water.

Suitably, at least about 5 wt % (or about 20%, about 50% or about 75%) of the active particles have a primary particle size greater than about 100 nm, and suitably the formulations produce a minimal residual whitening effect when applied to a skin surface. Suitably the formulations comprise about 0.05% to about 1.0% iron oxide particles having a primary particle size of less than about 50 nm.

Also provided are foamable sunscreen formulations comprising:
active particles comprising titanium dioxide particles having a primary particle size of greater than about 100 nm and zinc oxide particles having a primary particle size of greater than about 100 nm;
about 1% microcrystalline cellulose and about 0.2% cellulose gum; about 16% $C_{12-15}$ alkyl benzoate, about 1% octyldodecyl neopentanoate, about 1% butyl octyl salicylate;
about 1.2% glyceryl stearate, about 0.5% ceteareth-20, and about 2% polysorbate 80;
about 1.8% polyhydroxystearic acid and about 2.7% methyl methacrylate crosspolymer;
about 0.8% polyurethane-2, about 0.3% polymethyl methacrylate and about 0.6% tricontanyl PVP film;
iron oxide particles comprising red iron oxide particles, yellow iron oxide particles or black iron oxide particles, and mixtures thereof and about 50% to about 60% water.

Suitably the formulations produce a minimal residual whitening effect when applied to a skin surface. In embodiments, the formulations comprise about 0.05% to about 1.0% iron oxide particles having a primary particle size of less than about 50 nm.

It should be noted that for formulations comprising titanium dioxide particles and zinc oxide particles having a primary particle size larger than about 100 nm that the formulations can also further comprise titanium dioxide or zinc oxide particles having a primary particle size of less than about 100 nm, suitably less than about 50 nm, as described herein. In additional embodiments, formulations that comprise titanium dioxide particles and zinc oxide particles having a primary particle size larger than about 100 nm can specifically exclude titanium dioxide particles and zinc oxide particles having a primary particle size less than 100 nm or less than 50 nm.

Also provided herein are methods of preventing sun damage to a patient's skin surface, comprising applying the foamable sunscreen formulations described throughout topically to the surface of the skin.

As used herein "preventing sun damage" means that the formulations described throughout provide a sufficient barrier to the UVA and/or UVB radiation of the sun so as to reduce, limit or suitably eliminate, damage (i.e., degradation, mutations, skin burn) to cells, tissues, nucleic acids (DNA/RNA), etc. caused by the exposure of a skin surface to such radiation.

In exemplary embodiments, the foamable sunscreen formulations are applied at least once a day. Suitably, such formulations are applied on an as-needed basis throughout the day according to a patient's exposure to sun or other forms of UVA/UVB radiation.

As described herein, the foamable sunscreen formulations are suitably applied to any skin surface, including for example, the arms, face, legs, legs, chest, trunk or hands.

In further embodiments, foamable sunscreen formulations are provided that consist of or consist essentially of the recited components at the recited amounts.

In formulations that consist essentially of the recited ingredients, such formulations specifically exclude other sun-blocking agents, as the addition of such agents would be considered a material alteration to such formulations and is thus excluded from such formulations that consist essentially of the recited ingredients at the recited amounts.

It will be readily apparent to one of ordinary skill in the relevant arts that other suitable modifications and adaptations to the methods and applications described herein can be made without departing from the scope of any of the embodiments. The following examples are included herewith for purposes of illustration only and are not intended to be limiting.

EXAMPLES

Example 1: Exemplary Formulations Comprising Particles Less than 100 nm

Below are examples of stable/non-separating formulations containing only zinc oxide particles, only titanium dioxide particles, and a combination of both zinc oxide and titanium dioxide particles as active ingredients. Suitably, the zinc oxide have a primary particle size of 20 nm and the titanium dioxide particles have a primary particle size of 30 nm.

| | Formulation | | |
|---|---|---|---|
| Ingredient | #1 Wt % | #2 Wt % | #3 Wt % |
| Water | qs to 100% | qs to 100% | qs to 100% |
| Microcrystalline Cellulose | 1.0 | 1.0 | 1.0 |
| Cellulose Gum | 0.2 | 0.2 | 0.2 |
| Polyurethane-2 | 0.8 | 0.8 | 0.8 |
| Polymethyl Methacrylate | 0.3 | 0.3 | 0.3 |
| $C_{12-14}$ Alkyl Benzoate | 16.0 | 16.0 | 16.0 |
| Octodecyl Neopentanoate | 1.0 | 1.0 | 1.0 |
| Butyl Octyl Salicylate | 1.0 | 1.0 | 1.0 |
| Cetearyl Alcohol | 1.5 | 1.5 | 1.5 |
| Gyceryl Stearate | 1.3 | 1.3 | 1.3 |
| Ceteareth-20 | 0.5 | 0.5 | 0.5 |
| Polysorbate 80 | 2.0 | 2.0 | 2.0 |
| Polyhydroxystearic acid | 1.8 | 1.8 | 1.8 |
| Glycereth-26 | 0.5 | 0.5 | 0.5 |
| Tricontanyl PVP | 0.5 | 0.5 | 0.5 |

-continued

| Ingredient | Formulation #1 Wt % | #2 Wt % | #3 Wt % |
|---|---|---|---|
| Zinc Oxide | 10.0 | — | 10.0 |
| Titanium Dioxide | — | 3.0 | 3.0 |
| Methyl Methacrylate Crosspolymer | 2.8 | 2.8 | 2.8 |
| Preservative | 1.0 | 1.0 | 1.0 |

Zinc Oxide was obtained from Kobo Products, Inc., South Plainfield, N.J. Titanium Dioxide was obtained from Sensient Technologies, Milwaukee. Wis.

These formulations when aerosolized and applied to the skin, do not leave a white residue visible to the naked eye, i.e., they produce a minimal residual whitening effect.

Below are examples of stable/non-separating formulations containing only zinc oxide particles, only titanium dioxide particles, and a combination of both zinc oxide and titanium dioxide particles as active ingredients, and also containing iron oxide pigments to add color to the formulation to match appropriate skin tones. Suitably, the zinc oxide particles have a primary particle size of 20 nm and the titanium dioxide particles have a primary particle size of 30 nm.

| Ingredient | Formulation #4 Wt % | #5 Wt % | #6 Wt % |
|---|---|---|---|
| Water | qs to 100% | qs to 100% | qs to 100% |
| Microcrystalline Cellulose | 1.0 | 1.0 | 1.0 |
| Cellulose Gum | 0.2 | 0.2 | 0.2 |
| Polyurethane-2 | 0.8 | 0.8 | 0.8 |
| Polymethyl Methacrylate | 0.3 | 0.3 | 0.3 |
| $C_{12-14}$ Alkyl Benzoate | 16.0 | 16.0 | 16.0 |
| Octodecyl Neopentanoate | 1.0 | 1.0 | 1.0 |
| Butyl Octyl Salicylate | 1.0 | 1.0 | 1.0 |
| Cetearyl Alcohol | 1.5 | 1.5 | 1.5 |
| Gyceryl Stearate | 1.3 | 1.3 | 1.3 |
| Ceteareth-20 | 0.5 | 0.5 | 0.5 |
| Polysorbate 80 | 2.0 | 2.0 | 2.0 |
| Polyhydroxystearic acid | 1.8 | 1.8 | 1.8 |
| Glycereth-26 | 0.5 | 0.5 | 0.5 |
| Tricontanyl PVP | 0.5 | 0.5 | 0.5 |
| Zinc Oxide | 10.0 | — | 10.0 |
| Titanium Dioxide | — | 3.0 | 3.0 |
| Methyl Methacrylate Crosspolymer | 2.8 | 2.8 | 2.8 |
| Preservative | 1.0 | 1.0 | 1.0 |
| Iron Oxide Red CI 77491 | 0.12 | 0.12 | 0.12 |
| Iron Oxide Yellow CI 77492 | 0.3 | 0.3 | 0.3 |
| Iron Oxide Black | 0.05 | 0.05 | 0.05 |

Zinc Oxide was obtained from Kobo Products, Inc., South Plainfield, N.J. Titanium Dioxide was obtained from Sensient Technologies, Milwaukee, Wis.

These formulations when aerosolized and applied to the skin, do not leave a white residue visible to the naked eye, i.e., they produce a minimal residual whitening effect. The red, yellow, and black iron oxide pigments can be adjusted in any proportion or eliminated entirely as illustrated above to match skin tones based on the Fitzpatrick Skin Prototype Scale. The Fitzpatrick scale is the common reference in dermatology for classifying skin tone from very light (SPT I) to very dark (SPT VI). This scale is given below:

Classification of Fitzpatrick's Skin Prototypes

| SPT | Basic Skin Color | Response to Sun Exposure |
|---|---|---|
| I | Pale White | Does not tan, burns easily |
| II | White | Tan with difficulty, burns easily |
| III | White | Tan after initial sunburn |
| IV | Lt. Brown/Olive | Tan easily |
| V | Brown | Tan easily |
| VI | Black | Become darker |

Example 2: Exemplary Formulations Comprising Particles Greater than 100 nm

Provided below are formulations utilizing active particles comprising zinc oxide particles having a primary particle size greater than about 100 nm and titanium dioxide particles having a primary particle size of about 30 nm. These formulations demonstrate the use of iron oxide particles to match several skin tones on the Fitzpatrick Skin Prototype classification by modifying the amounts or red, yellow and black iron oxide particles.

| Ingredient | Wt % | Wt % | Wt % |
|---|---|---|---|
| Water | qs to 100% | qs to 100% | qs to 100% |
| Microcrystalline Cellulose | 1.0 | 1.0 | 1.0 |
| Cellulose Gum | 0.2 | 0.2 | 0.2 |
| Polyurethane-2 | 0.8 | 0.8 | 0.8 |
| Polymethyl Methacrylate | 0.3 | 0.3 | 0.3 |
| $C_{12-14}$ Alkyl Benzoate | 16.0 | 16.0 | 16.0 |
| Octodecyl Neopentanoate | 1.0 | 1.0 | 1.0 |
| Butyl Octyl Salicylate | 1.0 | 1.0 | 1.0 |
| Cetearyl Alcohol | 1.5 | 1.5 | 1.5 |
| Gyceryl Stearate | 1.3 | 1.3 | 1.3 |
| Ceteareth-20 | 0.5 | 0.5 | 0.5 |
| Polysorbate 80 | 2.0 | 2.0 | 2.0 |
| Polyhydroxystearic acid | 1.8 | 1.8 | 1.8 |
| Glycereth-26 | 0.5 | 0.5 | 0.5 |
| Tricontanyl PVP | 0.5 | 0.5 | 0.5 |
| Zinc Oxide (>100 nm) | 10.0 | 10.0 | 10.0 |
| Zinc Oxide (<100 nm) | — | — | — |
| Titanium Dioxide (>100 nm) | — | — | — |
| Titanium Dioxide (28-32 nm) | 3.0 | 3.0 | 3.0 |
| Methyl Methacrylate Crosspolymer | 2.8 | 2.8 | 2.8 |
| Preservative | 1.0 | 1.0 | 1.0 |
| Iron Oxide Red CI 77491 | 0.13 | 0.36 | 0.65 |
| Iron Oxide Yellow CI 77492 | 0.23 | 0.72 | 1.43 |
| Iron Oxide Black | 0.03 | 0.19 | 0.21 |

The mean primary particle size of the zinc oxide particles was about 380 nm, with a range of about 150 nm to about 550 nm.

Zinc Oxide was obtained from BASF Corp., Florham Park, N.J. Titanium Dioxide was obtained from Sensient Technologies, Milwaukee, Wis.

Results in matching the skin tone to the Fitzpatrick Skin Prototype classification are given in the table below.

| Formulation Number | Shade | Fitzpatrick Skin Prototype Match |
|---|---|---|
| 7 | Light | I to II * |
| 8 | Medium | II to III* |
| 9 | Darker | Greater than III* |

These formulations utilize 76.9% of the total amount of Titanium Dioxide and Zinc Oxide (active particles) having a primary particle size greater than about 100 nanometers. Skin tone can be matched to any desired shade by adjusting the amounts and combinations of the iron oxide pigments.

Provided below are formulations utilizing active particles comprising titanium dioxide particles having a primary particle size greater than about 100 nm and zinc oxide particles having a primary particle size of about 30 nm. These formulations demonstrate the use of iron oxide particles to match several skin tones on the Fitzpatrick Skin Prototype classification by modifying the amounts or red, yellow and black iron oxide particles.

| | Formulation | | |
|---|---|---|---|
| Ingredient | #10 Wt % | #11 Wt % | #12 Wt % |
| Water | qs to 100% | qs to 100% | qs to 100% |
| Microcrystalline Cellulose | 1.0 | 1.0 | 1.0 |
| Cellulose Gum | 0.2 | 0.2 | 0.2 |
| Polyurethane-2 | 0.8 | 0.8 | 0.8 |
| Polymethyl Methacrylate | 0.3 | 0.3 | 0.3 |
| $C_{12-14}$ Alkyl Benzoate | 16.0 | 16.0 | 16.0 |
| Octodecyl Neopentanoate | 1.0 | 1.0 | 1.0 |
| Butyl Octyl Salicylate | 1.0 | 1.0 | 1.0 |
| Cetearyl Alcohol | 1.5 | 1.5 | 1.5 |
| Gyceryl Stearate | 1.3 | 1.3 | 1.3 |
| Ceteareth-20 | 0.5 | 0.5 | 0.5 |
| Polysorbate 80 | 2.0 | 2.0 | 2.0 |
| Polyhydroxystearic acid | 1.8 | 1.8 | 1.8 |
| Glycereth-26 | 0.5 | 0.5 | 0.5 |
| Tricontanyl PVP | 0.5 | 0.5 | 0.5 |
| Zinc Oxide (>100 nm) | — | — | — |
| Zinc Oxide (30 nm) | 10.0 | 10.0 | 10.0 |
| Titanium Dioxide (>100 nm) | 3.0 | 3.0 | 3.0 |
| Titanium Dioxide (28-32 nm) | — | — | — |
| Methyl Methacrylate Crosspolymer | 2.8 | 2.8 | 2.8 |
| Preservative | 1.0 | 1.0 | 1.0 |
| Iron Oxide Red CI 77491 | 0.13 | 0.36 | 0.65 |
| Iron Oxide Yellow CI 77492 | 0.23 | 0.72 | 1.43 |
| Iron Oxide Black | 0.03 | 0.19 | 0.21 |

The mean primary particle size of the titanium dioxide particles was about 1100 nm, with a range of about 150 nm to about 10,000 nm.

Zinc Oxide was obtained from Kobo Products, Inc., South Plainfield, N.J. Titanium Dioxide was obtained from Kobo Products, Inc., South Plainfield, N.J.

Results in matching the skin tone to the Fitzpatrick Skin Prototype classification are given in the table below.

| Formulation Number | Shade | Fitzpatrick Skin Prototype Match |
|---|---|---|
| 10 | Light | I to II * |
| 11 | Medium | II to III* |
| 12 | Darker | Greater than III* |

These formulations utilize 23.1% of the total amount of Titanium Dioxide and Zinc Oxide (active particles) having a primary particle size greater than about 100 nanometers. The overall residual whiteness is less than that of formulations #'s 7, 8 & 9 above. Skin tone can be matched to any desired shade by adjusting the amounts and combinations of the iron oxide pigments.

Provided below are formulations utilizing active particles comprising titanium dioxide particles having a primary particle size greater than 100 nm and zinc oxide particles having a primary particle size greater than 100 nm. These formulations demonstrate the use of iron oxide particles to match several skin tones on the Fitzpatrick Skin Prototype classification by modifying the amounts or red, yellow and black iron oxide particles.

| | Formulation | | |
|---|---|---|---|
| Ingredient | #13 Wt % | #14 Wt % | #15 Wt % |
| Water | qs to 100% | qs to 100% | qs to 100% |
| Microcrystalline Cellulose | 1.0 | 1.0 | 1.0 |
| Cellulose Gum | 0.2 | 0.2 | 0.2 |
| Polyurethane-2 | 0.8 | 0.8 | 0.8 |
| Polymethyl Methacrylate | 0.3 | 0.3 | 0.3 |
| $C_{12-14}$ Alkyl Benzoate | 16.0 | 16.0 | 16.0 |
| Octodecyl Neopentanoate | 1.0 | 1.0 | 1.0 |
| Butyl Octyl Salicylate | 1.0 | 1.0 | 1.0 |
| Cetearyl Alcohol | 1.5 | 1.5 | 1.5 |
| Gyceryl Stearate | 1.3 | 1.3 | 1.3 |
| Ceteareth-20 | 0.5 | 0.5 | 0.5 |
| Polysorbate 80 | 2.0 | 2.0 | 2.0 |
| Polyhydroxystearic acid | 1.8 | 1.8 | 1.8 |
| Glycereth-26 | 0.5 | 0.5 | 0.5 |
| Tricontanyl PVP | 0.5 | 0.5 | 0.5 |
| Zinc Oxide (>100 nm) | 10.0 | 10.0 | 10.0 |
| Zinc Oxide (30 nm) | — | — | — |
| Titanium Dioxide (>100 nm) | 3.0 | 3.0 | 3.0 |
| Titanium Dioxide (28-32 nm) | — | — | — |
| Methyl Methacrylate Crosspolymer | 2.8 | 2.8 | 2.8 |
| Preservative | 1.0 | 1.0 | 1.0 |
| Iron Oxide Red CI 77491 | 0.13 | 0.36 | 0.65 |
| Iron Oxide Yellow CI 77492 | 0.23 | 0.72 | 1.43 |
| Iron Oxide Black | 0.03 | 0.19 | 0.21 |

The mean primary particle size of the zinc oxide particles was about 380 nm, with a range of about 150 nm to about 550 nm.

The mean primary particle size of the titanium dioxide particles was about 1100 nm, with a range of about 150 nm to about 10,000 nm.

Zinc Oxide was obtained from BASF Corp., Florham Park, N.J. Titanium Dioxide was obtained from Kobo Products, Inc., South Plainfield, N.J.

Results in matching the skin tone to the Fitzpatrick Skin Prototype classification are given in the table below.

| Formulation Number | Shade | Fitzpatrick Skin Prototype Match |
|---|---|---|
| 13 | Light | I to II * |
| 14 | Medium | II to III* |
| 15 | Darker | Greater than III* |

These formulations utilize 100.0% of the total amount of Titanium Dioxide and Zinc Oxide (active particles) having a primary particle size greater than about 100 nanometers, therefore the overall residual whiteness is darker than that of formulations described above (Formulations #:7-12). Skin tone can be matched to any desired shade by adjusting the amounts and combinations of the iron oxide pigments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

What is claimed is:

1. A sunscreen formulation consisting essentially of:
   a. about 1 wt % to about 25 wt % active particles having a primary particle size of about 10 nm to about 500 nm;
   b. about 0.1 wt % to about 20 wt % emulsion stabilizer;
   c. about 0.01 wt % to about 30 wt % skin conditioner;
   d. about 0.01 wt % to about 20 wt % emulsifier; and
   e. about 0.05 wt % to about 20 wt % suspending agent,
   wherein the formulation produces a minimal residual whitening effect when applied to a skin surface.

2. The sunscreen formulation of claim 1, wherein the active particles have a primary particle size of about 10 nm to about 200 nm.

3. The sunscreen formulation of claim 1, wherein the active particles comprise titanium dioxide particles, zinc oxide particles, or both.

4. The sunscreen formulation of claim 1, wherein the active particles comprise about 1 wt % to about 10 wt % titanium dioxide particles.

5. The sunscreen formulation of claim 1, wherein the active particles comprise about 1 wt % to about 20 wt % zinc oxide particles.

6. The sunscreen formulation of claim 1, wherein the active particles comprise about 1 wt % to about 10 wt % titanium dioxide particles and about 1 wt % to about 10 wt % zinc oxide particles.

7. The sunscreen formulation of claim 1, wherein the emulsion stabilizer is selected from microcrystalline cellulose, cellulose gum, xanthan gum, magnesium aluminum silicate, bentonite clay, hectorite clay, and combination thereof.

8. The sunscreen formulation of claim 1, wherein the skin conditioner is selected from $C_{12-15}$ alkyl benzoate, octyldodecyl neopentanoate, butyl octyl salicylate, caprylyl glycol, glycerin, fatty acid esters of $C_8$ or greater, mineral oil, and combination thereof.

9. The sunscreen formulation of claim 1, wherein the emulsifier is selected from glyceryl stearate, ceteareth-20, polysorbate 80, sodium lauryl sulfate, lecithin, and combination thereof.

10. The sunscreen formulation of claim 1, wherein the suspending agent is selected from polyhydroxystearic acid, sodium polyacrylate polymer, methyl methacrylate crosspolymer, and combination thereof.

11. The sunscreen formulation of claim 1, further consisting essentially of about 0.01 wt % to about 1 wt % iron oxide particles.

12. The sunscreen formulation of claim 1, further consisting essentially of a film former.

13. The sunscreen formulation of claim 12, wherein the film former is selected from polyurethane-2, polymethyl methacrylate, tricontanyl poly(vinyl pyrollidone) (PVP), vinyl pyrollidone/eicosene copolymer, and combination thereof.

14. A sunscreen formulation consisting essentially of:
   a. about 1 wt % to about 25 wt % zinc oxide particles having a primary particle size of about 10 nm to about 500 nm; about 1 wt % to about 25 wt % titanium dioxide particles having a primary particle size of about 10 nm to about 500 nm; or a combination thereof;
   b. an emulsion stabilizer;
   c. a skin conditioner;
   d. an emulsifier; and
   e. a suspending agent,
   wherein the formulation produces a minimal residual whitening effect when applied to a skin surface.

15. The sunscreen formulation of claim 14, wherein the emulsion stabilizer is selected from microcrystalline cellulose, cellulose gum, xanthan gum, magnesium aluminum silicate, bentonite clay, hectorite clay, and combination thereof.

16. The sunscreen formulation of claim 14, wherein the skin conditioner is selected from $C_{12-15}$ alkyl benzoate, octyldodecyl neopentanoate, butyl octyl salicylate, caprylyl glycol, glycerin, fatty acid esters of $C_8$ or greater, mineral oil, and combination thereof.

17. The sunscreen formulation of claim 14, wherein the emulsifier is selected from glyceryl stearate, ceteareth-20, polysorbate 80, sodium lauryl sulfate, lecithin, and combination thereof.

18. The sunscreen formulation of claim 14, wherein the suspending agent is selected from polyhydroxystearic acid, sodium polyacrylate polymer, methyl methacrylate crosspolymer, and combination thereof.

19. A sunscreen formulation consisting essentially of:
   a. about 1 wt % to about 25 wt % zinc oxide particles having a primary particle size of about 10 nm to about 500 nm; about 1 wt % to about 25 wt % titanium dioxide particles having a primary particle size of about 10 nm to about 500 nm; or a combination thereof;
   b. about 0.1 wt % to about 20 wt % emulsion stabilizer;
   c. about 0.01 wt % to about 30 wt % skin conditioner; and
   d. about 0.01 wt % to about 20 wt % emulsifier,
   wherein the formulation produces a minimal residual whitening effect when applied to a skin surface.

20. The sunscreen formulation of claim 19, further consisting essentially of a suspending agent, a film former, or both.

* * * * *